United States Patent
Kunin

(10) Patent No.: US 10,744,138 B2
(45) Date of Patent: *Aug. 18, 2020

(54) COMBINED HAIR LOSS INHIBITION TREATMENT

(71) Applicant: Beautopia LLC, New York, NY (US)

(72) Inventor: David Ben Kunin, New York, NY (US)

(73) Assignee: GARUHDA LLC, Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/265,410

(22) Filed: Feb. 1, 2019

(65) Prior Publication Data
US 2019/0160065 A1 May 30, 2019

Related U.S. Application Data

(63) Continuation of application No. 15/521,450, filed as application No. PCT/US2015/057126 on Oct. 23, 2015, now Pat. No. 10,195,199.

(60) Provisional application No. 62/068,370, filed on Oct. 24, 2014.

(51) Int. Cl.
| | | |
|---|---|---|
| *A61K 8/49* | (2006.01) | |
| *A61K 8/97* | (2017.01) | |
| *A61Q 7/00* | (2006.01) | |
| *A61K 36/21* | (2006.01) | |
| *A61K 31/505* | (2006.01) | |
| *A61K 31/506* | (2006.01) | |
| *A61K 36/235* | (2006.01) | |
| *A61P 17/14* | (2006.01) | |

(52) U.S. Cl.
CPC .......... *A61K 31/506* (2013.01); *A61K 8/4953* (2013.01); *A61K 8/97* (2013.01); *A61K 31/505* (2013.01); *A61K 36/21* (2013.01); *A61K 36/235* (2013.01); *A61P 17/14* (2018.01); *A61Q 7/00* (2013.01); *A61K 2800/5922* (2013.01)

(58) Field of Classification Search
CPC ........ A61K 31/506; A61K 8/97; A61K 8/495; A61K 31/505; A61K 36/21; A61K 26/235; A61K 2800/592; A61Q 7/00; A61P 17/14
See application file for complete search history.

(56) References Cited

U.S. PATENT DOCUMENTS

| | | | |
|---|---|---|---|
| 5,422,100 A | 6/1995 | Eliaz et al. | |
| 5,620,980 A * | 4/1997 | Samour | A61K 8/4953 514/256 |
| 5,620,982 A | 4/1997 | Wren | |
| 2002/0048558 A1 | 4/2002 | Niemiec et al. | |
| 2003/0176303 A1 | 9/2003 | Niemiec et al. | |
| 2007/0141015 A1 | 6/2007 | Malek | |
| 2008/0118458 A1 * | 5/2008 | Giesen | A61K 8/44 424/74 |
| 2008/0152731 A1 | 6/2008 | Trigiante | |
| 2009/0104295 A1 | 4/2009 | Kohno | |
| 2011/0117045 A1 | 5/2011 | Aimi et al. | |
| 2012/0258972 A1 | 10/2012 | Rafi et al. | |

FOREIGN PATENT DOCUMENTS

| | | |
|---|---|---|
| AU | 2011100917 A4 | 9/2011 |
| CN | 1303263 A | 7/2001 |
| EP | 2702982 A2 | 3/2014 |
| WO | 9742964 A1 | 11/1997 |
| WO | 2008028772 A1 | 3/2008 |
| WO | 2011031990 A1 | 3/2011 |

OTHER PUBLICATIONS

Donia Abd El Raheim M "Phytochemical Content and Antibacterial Activity of Atriplex Nummularia Extracts" Int J Biol Pharm Allied Sci 2(6):1260-1269, Jun. 2013.
Winter Ruth "A Consumer's Dictionary of Cosmetic Ingredients—Complete Information About the Harmful and Desirable Ingredients Found in Cosmetics and Cosmeceuticals" Three Rivers Press, 2009, 5 pages.
European Patent Application No. 15852368.8 Extended European Search Report dated Mar. 12, 2018, 10 pages.
International Patent Application No. PCT/US2015/057126 International Search Report and Written Opinion dated Jan. 15, 2016, 7 pages.
International Patent Application No. PCT/US2015/057126 International Preliminary Report on Patentability dated Apr. 25, 2017, 6 pages.
English translation of the IL Office Action for Patent Application 251862; dated Nov. 26, 2019; 3 pages.
Chinese Office Action for CN 201580070662.9; dated; 14 pages.
English translation of Chinese Office Action for CN 201580070662.9; 23 pages.
Indian Office Action for Application No. 201717017290; dated Jan. 22, 2019; 7 pages.

* cited by examiner

*Primary Examiner* — Shirley V Gembeh

(74) *Attorney, Agent, or Firm* — Morgan, Lewis & Bockius LLP

(57) ABSTRACT

A hair growth formulation includes minoxidil and foeniculum vulgare, atriplex nummularia extract, or a combination of foeniculum vulgare and atriplex nummularia extract. A method for increasing hair growth includes applying a hair growth formulation to a subject.

8 Claims, No Drawings

COMBINED HAIR LOSS INHIBITION TREATMENT

CROSS-REFERENCE TO RELATED APPLICATION

This application is a continuation of U.S. patent application Ser. No. 15/521,450, filed on Apr. 24, 2017, which is a U.S. National Stage of International Patent Application Serial No. PCT/US2015/057126, filed Oct. 23, 2015, which claims the benefit of U.S. Provisional Application Ser. No. 62/068,370, filed Oct. 24, 2014, each of which is incorporated by reference in its entirety.

BACKGROUND OF THE INVENTION

According to The Washington Post, American hair loss sufferers spend more than 3.5 billion dollars a year in an attempt to treat hair loss. Unfortunately, many of the products being marketed hair loss treatment industry are ineffective for the majority of those who use them.

The American Hair Loss Association (AHLA) recognizes that hair loss is an extremely emotionally distressing disease that can make those afflicted particularly vulnerable. For this reason, The AHLA recommends against purchasing any hair loss product that is not approved or recommended by the FDA. It is the present inventor's understanding that only product that has been approved by the FDA for the treatment hair loss is minoxidil.

Although minoxidil compositions have been proven to have a certain level of effectiveness, the present invention addresses problems and limitations associated with known hair growth and re-growth treatments.

SUMMARY OF THE INVENTION

According to some embodiments of the invention, a hair growth formulation comprises minoxidil and foeniculum vulgare, atriplex nummularia extract, or a combination of foeniculum vulgare and atriplex nummularia extract. In some embodiments a hair growth formulation comprises minoxidil and foeniculum vulgare and in some embodiments the minoxidil and foeniculum vulgare are present in a ratio of about 1:1. In some embodiments a hair growth formulation comprises minoxidil and atriplex nummularia extract and in some embodiments the minoxidil and atriplex nummularia extract are present in a ratio of about 1:1. In some embodiments a hair growth formulation comprises minoxidil, foeniculum vulgare, and atriplex nummularia extract and in some embodiments the foeniculum vulgare and atriplex nummularia extract are present in a ratio of about 1:1. In some embodiments the formulation further comprises a dihydrotestosterone blocking agent.

According to some embodiments of the invention, a hair growth formulation comprises minoxidil and a dihydrotestosterone blocking agent. In some embodiments the dihydrotestosterone blocking agent comprises finasteride. In other embodiments the dihydrotestosterone blocking agent comprises dutaseride. In some embodiments the minoxidil and dihydrotestosterone blocking agent are present in a ratio of about 1:1.

In some embodiments the minoxidil is present at about 2% to about 5% by weight of the formulation. In some embodiments the formulation is a liquid, gel or foam.

According to some embodiments of the invention, a method for increasing hair growth comprises applying a hair growth formulation to a subject, wherein the hair growth formulation comprises minoxidil and foeniculum vulgare, atriplex nummularia extract, a dihydrotestosterone blocking agent, or a combination of two or more thereof. In some embodiments the hair growth formulation is applied twice a day. In some embodiments the hair growth formulation is a liquid, gel, or foam. In some embodiments the minoxidil is present in the hair growth formulation at about 2% to about 5% by weight of the total formulation.

DETAILED DESCRIPTION OF THE INVENTION

In some embodiments, formulations of the present invention are designed to increase hair growth or prevent or minimize the loss of existing hair. In some embodiments a hair growth formulation includes a piperidinopyrimidine derivative (e.g. minoxidil) and a second active agent. In some embodiments the second active agent includes foeniculum vulgare, atriplex nummularia extract, or a combination of foeniculum vulgare and atriplex nummularia extract. In other embodiments the second active agent includes a dihydrotestosterone blocker. In some embodiments the piperidinopyrimidine derivative and the second agent are provided in a single formulation, while in other embodiments the minoxidil and the second agent are provided in separate formulations.

Components
Active Ingredients

In some embodiments an active ingredient for use in the present invention can be a piperidinopyrimidine derivative, or an analog, homologue, polymorph, or salt thereof. In some embodiments a piperidinopyrimidine derivative can be minoxidil (also referred to as Rogaine® or 6-piperidin-1-ylpyrimidine-2,4-diamine-3-oxide). An active ingredient for use in the present invention may have a chemical structure according to Formula 1:

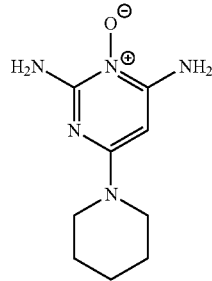

Formula 1

In some embodiments an active ingredient in a formulation of the present invention is foeniculum vulgare (also referred to as fennel), atriplex nummularia extract (also referred to as old man saltbush extract, bluegreen saltbush extract, and giant saltbush extract), or a derivative, analog, homologue, polymorph, salt, or combination thereof. In some embodiments "foeniculum vulgare" may be foeniculum vulgare extract. In other embodiments "foeniculum vulgare" may be any form of foeniculum vulgar, for example, seed, leaf, flower, bulb, or dried plant.

In some embodiments an active ingredient in a formulation of the present invention is a dihydrotestosterone (DHT) blocking agent. DHT blocking agents include finasteride (also known as Propecia® and Proscar®), dutaseride (also known as Avodart®), pygeum, nettles, pumpkin seed oil, green tea, emu oil, soy isoflavones, beta isosterols, In some embodiments a formulation of the present invention includes one or more active ingredients. In some embodiments a formulation of the present invention includes minoxidil and foeniculum vulgare. In some embodiments a formulation of the present invention includes minoxidil and atriplex nummularia extract. In some embodiments a formulation of the present invention includes minoxidil and a DHT blocking agent. In some embodiments a formulation of the present invention includes minoxidil and finasteride. In some embodiments a formulation of the present invention includes minoxidil and dutaseride.

Typically when processed into a suitable dosage form, as described in more detail below, the active ingredient, or each active ingredient, can be present in such dosage forms in an amount normally prescribed, typically about 2% to about 5% percent by weight, based on the total weight of the formulation. In some embodiments the active ingredient can be present in about 0.1% to about 90%, about 0.1% to about 80%, about 0.1% to about 70%, about 0.1% to about 60%, about 0.1% to about 50%, about 0.1% to about 40%, about 0.1% to about 30%, about 0.1% to about 25%, about 0.1% to about 20%, about 0.1% to about 15%, about 0.1% to about 10%, about 1% to about 10%, about 1% to about 5%, about 2% to about 5% by weight, about 3% to about 5% by weight, about 5% to about 15% by weight, about 7.5% to about 12% by weight, about 10% to about 90% by weight, about 10% to about 80% by weight, about 10% to about 70% by weight, about 10% to about 60% by weight, about 10% to about 50% by weight, about 10% to about 40% by weight, about 10% to about 30% by weight, about 10% to about 20% by weight, about 20% to about 90% by weight, about 20% to about 80% by weight, about 20% to about 70% by weight, about 20% to about 60% by weight, about 20% to about 50% by weight, about 20% to about 40% by weight, about 20% to about 30% by weight, about 30% to about 90% by weight, about 30% to about 80% by weight, about 30% to about 70% by weight, about 30% to about 60% by weight, about 30% to about 50% by weight, about 30% to about 40% by weight, about 40% to about 90% by weight, about 40% to about 80% by weight, about 40% to about 70% by weight, about 40% to about 60% by weight, about 40% to about 50% by weight, about 50% to about 90% by weight, about 50% to about 80% by weight, about 50% to about 70% by weight, about 50% to about 60% by weight, about 60% to about 90% by weight, about 60% to about 80% by weight, about 60% to about 70% by weight, about 70% to about 90% by weight, about 70% to about 80% by weight, about 80% to about 90% by weight, based on the total weight of the formulation. In some embodiments the active ingredient can be present in about 95% or less, about 90% or less, about 80% or less, about 70% or less, about 60% or less, about 50% or less, about 45% or less, about 40% or less, about 35% or less, about 30% or less, about 25% or less, about 20% or less, about 15% or less, about 10% or less, about 7% or less, or about 5% or less by weight, based on the total weight of the formulation.

In some embodiments a formulation comprises minoxidil or a derivative, analog, homologue, or polymorph thereof and foeniculum vulgare or a derivative, analog, homologue, or polymorph thereof. In such embodiments the minoxidil and foeniculum vulgare may be present in a ratio of about 50:1, about 40:1, about 30:1, about 25:1, about 20:1, about 15:1, about 10:1, about 8:1, about 5:1, about 4:1, about 3:1, about 2.5:1, about 2:1, about 1.5:1, about 1:2, about 1:2.5, about 1:3, about 1:4, about 1:5, about 1:8, about 1:10, about 1:15, about 1:20, about 1:25, about 1:30, about 1:40, or about 1:50 by weight or volume.

In some embodiments a formulation comprises minoxidil or a derivative, analog, homologue, or polymorph thereof and atriplex nummularia extract or a derivative, analog, homologue, or polymorph thereof. In such embodiments the minoxidil and atriplex nummularia extract may be present in a ratio of about 50:1, about 40:1, about 30:1, about 25:1, about 20:1, about 15:1, about 10:1, about 8:1, about 5:1, about 4:1, about 3:1, about 2.5:1, about 2:1, about 1.5:1, about 1:1, about 1:1.5, about 1:2, about 1:2.5, about 1:3, about 1:4, about 1:5, about 1:8, about 1:10, about 1:15, about 1:20, about 1:25, about 1:30, about 1:40, or about 1:50 by weight or volume.

In some embodiments a formulation comprises foeniculum vulgare or a derivative, analog, homologue, or polymorph thereof and atriplex nummularia extract or a derivative, analog, homologue, or polymorph thereof. In such embodiments the foeniculum vulgare and atriplex nummularia extract may be present in a ratio of about 50:1, about 40:1, about 30:1, about 25:1, about 20:1, about 15:1, about 10:1, about 8:1, about 5:1, about 4:1, about 3:1, about 2.5:1, about 2:1, about 1.5:1, about 1:1, about 1:1.5, about 1:2, about 1:2.5, about 1:3, about 1:4, about 1:5, about 1:8, about 1:10, about 1:15, about 1:20, about 1:25, about 1:30, about 1:40, or about 1:50 by weight or volume.

Additional Ingredients

The present invention can also optionally include other ingredients to enhance dosage form manufacture from a pharmaceutical composition of the present invention and/or alter the release profile of a dosage form including a pharmaceutical composition of the present invention.

Some embodiments of the present invention include one or more pharmaceutically acceptable fillers/diluents. Any suitable diluent may be used, including mineral oil, water and/or a lower alcohol. In some embodiments the lower alcohol can be methyl alcohol, ethyl alcohol, isopropyl alcohol, benzyl alcohol, SD alcohol 40, and mixtures thereof. In some embodiments a solvent is present in an amount of about 99% or less, about 95% or less, about 90% or less, about 80% or less, about 75% or less, about 70% or less, about 60% or less, or about 50% or less. In some embodiments a solvent is present in an amount of about 40% to about 95%, about 40% to about 90%, about 40% to about 80%, about 40% to about 75%, about 40% to about 70%, about 40% to about 60%, about 40% to about 50%, about 50% to about 99%, about 50% to about 95%, about 50% to about 90%, about 50% to about 80%, about 50% to about 75%, about 50% to about 70%, about 50% to about 60%, about 60% to about 95%, about 60% to about 90%, about 60% to about 80%, about 60% to about 75%, about 60% to about 70%, about 70% to about 95%, about 70% to about 90%, about 70% to about 80%, about 80% to about 95%, about 80% to about 90%. Some embodiments of the present invention may further include a co-solvent. Suitable co-solvents include aromatic alcohols, polyhydric alcohols, butylene glycol, hexylene glycol, ethoxydiglycol, dipropylene glycol, and mixtures thereof. In some embodiments a co-solvent is present in an amount of about 50% by weight or less, about 40% by weight or less, about 30% by weight or less, about 25% by weight or less, about 20% by weight or less, about 15% by weight or less, about 10% by weight or less, about 7.5% by weight or less, or about 5% by weight or less.

In some embodiments, the present invention can include one or more stabilizers. Any suitable stabilizer may be used, including carbomers, ethanolamine, diethanolamine, triethanolamine, and mixtures thereof. In some embodiments a stabilizer can be present in an amount of about 50% by weight or less, about 40% by weight or less, about 30% by weight or less, about 25% by weight or less, about 20% by weight or less, about 15% by weight or less, about 10% by weight or less, or about 5% by weight or less. In some embodiments a stabilizer can be present in an amount of about 0.1% to about 50% by weight, about 0.1% to about 40% by weight, about 0.1% to about 30% by weight about 0.1% to about 25% by weight, about 0.1% to about 20% by weight, about 0.1% to about 15% by weight, about 0.1% to about 10% by weight, about 0.1% to about 5% by weight, about 1% to about 50% by weight, about 1% to about 40% by weight, about 1% to about 30% by weight about 1% to about 25% by weight, about 1% to about 20% by weight, about 1% to about 15% by weight, about 1% to about 10% by weight, about 1% to about 5% by weight, about 5% to about 50% by weight, about 5% to about 40% by weight, about 5% to about 30% by weight about 5% to about 25% by weight, about 5% to about 20% by weight, about 05% to about 15% by weight, about 5% to about 10% by weight, about 0.1% to about 50% by weight, about 10% to about 40% by weight, about 10% to about 30% by weight about 10% to about 25% by weight, about 10% to about 20% by weight, about 10% to about 15% by weight, about 15% to about 50% by weight, about 15% to about 40% by weight, about 15% to about 30% by weight about 15% to about 25% by weight, about 15% to about 20% by weight, about 20% to about 50% by weight, about 20% to about 40% by weight, about 20% to about 30% by weight about 20% to about 25% by weight, about 30% to about 50% by weight, about 30% to about 40% by weight, or about 40% to about 50% by weight.

In some embodiments, the present invention can include one or more preservatives. Any suitable preservative may be used, including benzalkonium chloride, benzethonium chloride, benzyl alcohol, bronopol, cetrimide, cetylpyridinium chloride, chlorhexidine, chlorobutanol, chlorocresol, chloroxylenol, chlorphenesin, cresol, ethyl alcohol, glycerin, hexetidine, imidurea, phenol, phenoxyethanol, phenylethyl alcohol, phenylmercuric nitrate, propylene glycol, thimerosal, butyl paraben, methylparaben, ethyl paraben, propyl paraben, benzoic acid, potassium sorbate, sodium benzoate, sodium propionate, sorbic acid, or mixtures thereof. Chlorphenesin, phenoxyethanol, sorbic acid and/or benzoic are preferred in some embodiments. In some embodiments a preservative can be present in an amount of about 50% by weight or less, about 40% by weight or less, about 30% by weight or less, about 25% by weight or less, about 20% by weight or less, about 15% by weight or less, about 10% by weight or less, or about 5% by weight or less. In some embodiments a preservative can be present in an amount of about 0.1% to about 50% by weight, about 0.1% to about 40% by weight, about 0.1% to about 30% by weight about 0.1% to about 25% by weight, about 0.1% to about 20% by weight, about 0.1% to about 15% by weight, about 0.1% to about 10% by weight, about 0.1% to about 5% by weight, about 1% to about 50% by weight, about 1% to about 40% by weight, about 1% to about 30% by weight about 1% to about 25% by weight, about 1% to about 20% by weight, about 1% to about 15% by weight, about 1% to about 10% by weight, about 1% to about 5% by weight, about 5% to about 50% by weight, about 5% to about 40% by weight, about 5% to about 30% by weight about 5% to about 25% by weight, about 5% to about 20% by weight, about 05% to about 15% by weight, about 5% to about 10% by weight, about 0.1% to about 50% by weight, about 10% to about 40% by weight, about 10% to about 30% by weight about 10% to about 25% by weight, about 10% to about 20% by weight, about 10% to about 15% by weight, about 15% to about 50% by weight, about 15% to about 40% by weight, about 15% to about 30% by weight about 15% to about 25% by weight, about 15% to about 20% by weight, about 20% to about 50% by weight, about 20% to about 40% by weight, about 20% to about 30% by weight about 20% to about 25% by weight, about 30% to about 50% by weight, about 30% to about 40% by weight, or about 40% to about 50% by weight.

In some embodiments, the present invention can include one or more emollients. Any suitable emollient may be used, including butyl myristate, ethylhexylmyristate, ethyl myristate, glyceryl dimyristate, glyceryl isostearate/myristate, glyceryl myristate, isobutyl myristate, isodecyl myristate, isopropyl myristate, isostearyl myristate, methyl myristate, propylene glycol myristate, or mixtures thereof. In some embodiments an emollient can be present in an amount of about 50% by weight or less, about 40% by weight or less, about 30% by weight or less, about 25% by weight or less, about 20% by weight or less, about 15% by weight or less, about 10% by weight or less, or about 5% by weight or less. In some embodiments an emollient can be present in an amount of about 0.1% to about 50% by weight, about 0.1% to about 40% by weight, about 0.1% to about 30% by weight about 0.1% to about 25% by weight, about 0.1% to about 20% by weight, about 0.1% to about 15% by weight, about 0.1% to about 10% by weight, about 0.1% to about 5% by weight, about 1% to about 50% by weight, about 1% to about 40% by weight, about 1% to about 30% by weight about 1% to about 25% by weight, about 1% to about 20% by weight, about 1% to about 15% by weight, about 1% to about 10% by weight, about 1% to about 5% by weight, about 5% to about 50% by weight, about 5% to about 40% by weight, about 5% to about 30% by weight about 5% to about 25% by weight, about 5% to about 20% by weight, about 05% to about 15% by weight, about 5% to about 10% by weight, about 0.1% to about 50% by weight, about 10% to about 40% by weight, about 10% to about 30% by weight about 10% to about 25% by weight, about 10% to about 20% by weight, about 10% to about 15% by weight, about 15% to about 50% by weight, about 15% to about 40% by weight, about 15% to about 30% by weight about 15% to about 25% by weight, about 15% to about 20% by weight, about 20% to about 50% by weight, about 20% to about 40% by weight, about 20% to about 30% by weight about 20% to about 25% by weight, about 30% to about 50% by weight, about 30% to about 40% by weight, or about 40% to about 50% by weight.

In some embodiments, the present invention can include one or more skin penetration enhancers that increase absorption of the active ingredient through the skin. Any suitable skin penetration enhancer may be used, including isopropyl myristate, sulfoxides (e.g. dimethylsulfoxide), azones (e.g. laurocapram), pyrrolidones (e.g. 2-pyrrolidone), alcohols and alkanols (e.g. dodecanol, oleyl alcohol, propylene glycol, isopropyl alcohol), surfactants, fatty acids (e.g. lauric acid, myristic acid, capric acid, polyoxyethylene-2-oleyl ether, polyoxyethylene-2-stearyl ether), terpenes (e.g. found in essential oils such as eucalyptus, chenopodium and ylang-ylang), oxazolidinones (e.g. 4-decyloxazolidin-2-one), urea, or mixtures thereof. In some embodiments a penetration enhancer can be present in an amount of about 50% by weight or less, about 40% by weight or less, about 30% by weight or less, about 25% by weight or less, about 20% by weight or less, about 15% by weight or less, about 10% by weight or less, or about 5% by weight or less. In some embodiments a penetration enhancer can be present in an amount of about 0.1% to about 50% by weight, about 0.1% to about 40% by weight, about 0.1% to about 30% by weight about 0.1% to about 25% by weight, about 0.1% to about 20% by weight, about 0.1% to about 15% by weight, about 0.1% to about 10% by weight, about 0.1% to about 5% by weight, about 1% to about 50% by weight, about 1% to about 40% by weight, about 1% to about 30% by weight about 1% to about 25% by weight, about 1% to about 20% by weight, about 1% to about 15% by weight, about 1% to about 10% by weight, about 1% to about 5% by weight, about 5% to about 50% by weight, about 5% to about 40% by weight, about 5% to about 30% by weight about 5% to about 25% by weight, about 5% to about 20% by weight, about 05% to about 15% by weight, about 5% to about 10% by weight, about 0.1% to about 50% by weight, about 10% to about 40% by weight, about 10% to about 30% by weight about 10% to about 25% by weight, about 10% to about 20% by weight, about 10% to about 15% by weight, about 15% to about 50% by weight, about 15% to about 40% by weight, about 15% to about 30% by weight about 15% to about 25% by weight, about 15% to about 20% by weight, about 20% to about 50% by weight, about 20% to about 40% by weight, about 20% to about 30% by weight about 20% to about 25% by weight, about 30% to about 50% by weight, about 30% to about 40% by weight, or about 40% to about 50% by weight.

In some embodiments a formulation described herein may be in the form of a tablet. Such a tablet may comprise a first active ingredient and a second active ingredient as described herein, as well as one or more excipients. Excipients may include, for example, fillers, disintegrants, glidants, lubricants.

In one embodiment, Avicel PH (Microcrystalline cellulose) is a filler used in the formulation. The Avicel PH can have an average particle size ranging from 20 to about 200 μm, preferably about 100 μm. The density can range from about 1.512 to about 1.668 g/cm³. The Avicel PH should have molecular weight of about 36,000. Avicel PH effectiveness is optimal when it is present in an amount of from about 10 to 65 percent, by weight on a solid basis, of the formulation. Typical fillers can be present in amounts from 10 to 65 percent by weight on a dry weight basis of the total composition. Other ingredients can include sugars and/or polyols. Lactose having a particle size of about 20 to about 400 microns and a density of about 0.3 to about 0.9 g/ml can also be included.

In some embodiments of the invention, the fillers which can be present at about 10 to 65 percent by weight on a dry weight basis, also function as binders in that they not only impart cohesive properties to the material within the formulation, but can also increase the bulk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

In one embodiment, the present invention can include one or more pharmaceutically acceptable disintegrants. Such disintegrants are known to a skilled artisan. In the present invention, disintegrants can include, but are not limited to, sodium starch glycolate (Explotab®) having a particle size of about 104 microns and a density of about 0.756 g/ml, starch (e.g., Starch 21) having a particle size of about 2 to about 32 microns and a density of about 0.462 g/ml, Crospovidone® having a particle size of about 400 microns and a density of about 1.22 g/ml, and croscarmellose sodium (Ac-Di-Sol) having a particle size of about 37 to about 73.7 microns and a density of about 0.529 g/ml. The disintegrant selected should contribute to the compressibility, flowability and homogeneity of the formulation. Further the disintegrant can minimize segregation and provide an immediate release profile to the formulation. In some embodiments, the disintegrant(s) are present in an amount from about 2 to about 25 percent by weight on a solid basis of the directly compressible formulation. Furthermore, antacids added to the formulations may aid in tablet disintegration when the tablet is introduced to a low pH environment through the effervescence of the antacid ingredient, thus potentially reducing the requirement for additional disintegrants.

In one embodiment, the present invention can include one or more pharmaceutically acceptable glidants, including but not limited to colloidal silicon dioxide. In one embodiment, colloidal silicon dioxide (Cab-O-Sil®) having a density of about 0.029 to about 0.040 g/ml can be used to improve the flow characteristics of the formulation. Such glidants can be provided in an amount of from about 0.1 to about 1 percent by weight of the formulation on a solid basis. It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

In one embodiment, the present invention can include one or more pharmaceutically acceptable lubricants, including but not limited to magnesium stearate. In one embodiment, the magnesium stearate has a particle size of about 450 to about 550 microns and a density of about 1.00 to about 1.80 g/ml. In one embodiment, magnesium stearate can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In an embodiment of the present invention, magnesium stearate having a particle size of from about 5 to about 50 microns and a density of from about 0.1 to about 1.1 g/ml is used in a pharmaceutical composition. In certain embodiments, a lubricant should make up from about 0.1 to about 2 percent by weight of the formulation on a solid basis. Suitable lubricants are stable and do not polymerize within the formulation once combined. Other lubricants known in the art or to be developed which exhibit acceptable or comparable properties include stearic acid, hydrogenated oils, sodium stearyl fumarate, polyethylene glycols, and Lubritab®.

In some embodiments, a pharmaceutical composition may be prepared by intimately mixing the active ingredient with one or more excipients by any suitable process (i.e. dry or wet granulation, hot melt extrusion, etc.).

Suitable formulations and dosage forms of the present invention include but are not limited to liquids, lotions, gels, foams, creams, shampoos, powders, caplets, pills, suppositories, soft gelatin capsules, capsules and compressed tablets manufactured from a pharmaceutical composition of the present invention. The dosage forms can be any shape, including regular or irregular shape depending upon the needs of the artisan.

Compressed tablets including the pharmaceutical compositions of the present invention can be direct compression tablets or non-direct compression tablets. In one embodiment, a dosage form of the present invention can be made by wet granulation, and/or dry granulation (e.g., slugging or roller compaction). The method of preparation and type of excipients are selected to give the tablet formulation desired physical characteristics that allow for the rapid compression of the tablets. After compression, the tablets must have a number of additional attributes such as appearance, hardness, disintegrating ability, and an acceptable dissolution profile.

Choice of fillers and other excipients typically depend on the chemical and physical properties of the active ingredient(s), behavior of the mixture during processing, and the properties of the final formulation. Adjustment of such parameters is understood to be within the general understanding of one skilled in the relevant art. Suitable fillers and excipients are described in more detail above.

Methods for treating hair loss are provided herein. In some embodiments a method of treating hair loss comprises a method of increasing hair growth, a method of preventing or reducing hair loss, or a combination thereof. In some embodiments a method of treating hair loss comprises administration of a formulation described herein to a subject. In some embodiments the subject is a mammal, for example a human, rat, mouse, dog, pig or horse. In some embodiments administration of a formulation described herein comprises applying the formulation to the skin of the subject. In some embodiments a formulation described herein is applied once a month, once every two weeks, once every week, once every other day, daily, twice daily, or three times daily.

In some embodiments, the active ingredient, or each of the active ingredients of a formulation as described herein is administered in a dosage of about 1 mg/day, 2 mg/day, 5 mg/day, 10 mg/day, 20 mg/day, or 40 mg/day, or about 1 mg/day to about 5 mg/day, about 5 mg/day to about 10 mg/day, about 10 mg/day to about 20 mg/day, or about 20 mg/day to about 40 mg/day, in single or divided doses. In some embodiments, the active ingredient, or each of the active ingredients, is present in a dosage of 1 mL of a 2% solution or 1 mL of a 5% solution bis en die (b.i.d., i.e. twice daily). The exact dosage will depend upon the route of administration, the form in which the compound is administered, the gender and age of the subject to be treated, the body weight of the subject to be treated, and the preference and experience of an attending physician. Dosing may be once a month, once every two weeks, once every week, once every other day, daily, twice daily, or three times daily.

In some embodiments, a formulation as described herein is administered in a dosage of about 0.1 ml, about 0.5 ml, about 1 ml, about 1.5 ml, about 2 ml, about 2.5 ml, about 3 ml, about 3.5 ml, about 4 ml, about 4.5 ml, about 5 ml, about 6 ml, about 7 ml, about 8 ml, about 9 ml, about 10 ml, about 12 ml, about 15 ml, about 20 ml, about 25 ml, about 30 ml, about 40 ml, about 50 ml, about 60 ml, about 70 ml, about 80 ml, about 90 ml, about 100 ml, about 125 ml, about 150 ml, about 175 ml, about 200 ml, about 225 ml, about 250 ml, about 275 ml, about 300 ml, about 325 ml, about 350 ml, about 375 ml, about 400 ml, about 425 ml, about 450 ml, about 475 ml, or about 500 ml. In some embodiments a formulation described herein is administered in a dosage of about 0.1 ml to about 500 ml, about 0.1 ml to about 250 ml, about 0.1 ml to about 100 ml, about 0.1 ml to about 75 ml, about 0.1 to about 50 ml, about 0.1 to about 25 ml, about 0.1 to about 15 ml, about 0.1 to about 10 ml, about 0.1 to about 5 ml, about 0.1 to about 2.5 ml, about 0.1 to about 2 ml, about 0.1 to about 1 ml, about 1 ml to about 250 ml, about 1 ml to about 100 ml, about 1 ml to about 75 ml, about 1 ml to about 50 ml, about 1 ml to about 25 ml, about 1 ml to about 10 ml, about 1 ml to about 5 ml, about 5 ml to about 10 ml, about 5 ml to about 10 ml, about 5 ml to about 25 ml, about 10 ml to about 25 ml, about 10 ml to about 50 ml, about 10 ml to about 75 ml, about 10 ml to about 100 ml, about 25 ml to about 50 ml, about 25 ml to about 75 ml, about 25 ml to about 100 ml, about 25 ml to about 250 ml, about 50 ml to about 100 ml, about 50 ml to about 250 ml, about 50 ml to about 500 ml, about 100 ml to about 150 ml, about 100 ml to about 200 ml, about 100 ml to about 250 ml, about 100 ml to about 300 ml, about 100 ml to about 500 ml, or about 250 ml to about 500 ml.

In some embodiments a method of treating hair loss comprises administration of a first active agent and a second active agent. The first active agent and second active agent may be administered simultaneously (e.g. in a single formulation) or sequentially (e.g. about 10 seconds apart, about 20 seconds apart, about 30 seconds apart, about 1 minute apart, about 2 minutes apart, about 5 minutes apart, about 10 minutes apart, about 15 minutes apart, about 20 minutes apart, about 30 minutes apart, about 45 minutes apart, about 60 minutes apart, about 2 hours apart, about 4 hours apart, about 6 hours apart, about 8 hours apart, or about 12 hours apart). When administered sequentially, the first active agent and second active agent can be administered in any order.

In some embodiments the first agent comprises minoxidil. In some embodiments the second agent comprises foeniculum vulgare, atriplex nummularia extract, a dihydrotestosterone blocking agent, or a combination of two or more thereof. In some embodiments the second agent comprises foeniculum vulgare, atriplex nummularia extract, or a combination of two or more thereof. In some embodiments the second agent comprises a dihydrotestosterone blocking agent.

In some embodiments administration may refer to topical application. In some embodiments administration may refer to oral, subcutaneous, intravenous, intralymphatic, intranasal, transdermal, intraperitoneal, intramuscular, or transmucosal administration.

In some embodiments a formulation as described herein may be applied to a subject in conjunction with another therapy for treating hair loss. Other therapies that are suitable for use in conjunction with a formulation as described herein include massage therapy, laser therapy (e.g. a laser comb). Such therapies may be administered with a formulation as described herein simultaneously or sequentially.

As used herein, the term "about" is understood to mean±10% of the value referenced. For example, "about 45%" is understood to literally mean 40.5% to 49.5%.

As used herein, the term "bioequivalence" is understood to mean one or more of $C_{max}$, $T_{max}$, or area under the concentration curve "AUC" of a drug is within 75% to 120% of the same marker for a referenced drug.

It will be appreciated by persons skilled in the art that numerous variations and/or modifications may be made to the invention shown in the specific embodiments without departing from the spirit and scope of the invention as broadly described. Further, each and every reference cited above is hereby incorporated by reference as if fully set forth herein.

Example 1

A formulation in accordance with an embodiment of the invention is as follows:

| | |
|---|---|
| minoxidil | 1%-15% |
| water | 10%-90% |
| carbomer | 0.1%-10% |
| isopropyl myristate | 0.1%-10% |
| *foeniculum vulgare* | 1%-15% |
| SD alcohol 40 | 10%-90% |
| *atriplex nummularia* extract | 1%-15% |
| sulfur | 0.1%-10% |
| triethanolamine | 0.1%-10% |
| phenoxyethanol | 0.1%-10% |
| sorbic acid | 0.1%-10% |
| chlorphenesin | 0.1%-10% |
| benzoic acid | 0.1%-10% |
| butylene glycol | 0.1%-10% |

Example 2

A formulation in accordance with an embodiment of the invention is as follows: 3-5% by weight minoxidil and balance of formulation Hair Up Herbal Treatment available from Schulamit Cosmetics & Aerosol (1999) Ltd., 7 Hayuvalim St. Industrial Zone A Neve-Neeman 45247, P.O. Box 7275 Hod-Hasharon 4524 Israel. Hair Up Herbal Treatment contains the following ingredients: water, carbomer, isopropyl myristate, foeniculum vulgare, SD alcohol 40, atriplex nummularia extract, sulfur, triethanolamine, phenoxyethanol, sorbic acid, chlorphenesin, benzoic acid, and butylene glycol.

What is claimed is:

1. A method for increasing hair growth comprising:
   applying a hair growth formulation to a subject, wherein the hair growth formulations comprises:
   (a) minoxidil; and
   (b) atriplex nummularia extract.

2. The method according to claim 1, wherein the applying step is performed twice a day.

3. The method according to claim 1, wherein the hair growth formulation is a liquid, gel, or foam.

4. The method according to claim 1, wherein the minoxidil is present in the hair growth formulation at about 2% to about 5% by weight of the total formulation.

5. The method according to claim 1, wherein the hair growth formulation further comprises one or more of foeniculum vulgare and a dihydrotestosterone blocking agent.

6. The method according to claim 5, wherein the dihydrotestosterone blocking agent is dutasteride.

7. The method according to claim 1, wherein the atriplex nummularia extract and minoxidil are present in a ratio of about 1:1 by weight.

8. The method according to claim 5, wherein the formulation further comprises foeniculum vulgare in a ratio of 1:1 by weight with atriplex nummularia extract.

* * * * *